United States Patent [19]

Clifford et al.

[11] Patent Number: 4,529,819

[45] Date of Patent: Jul. 16, 1985

[54] METHOD FOR MAKING BENZOYLPHENYLUREAS

[75] Inventors: David P. Clifford; Robert A. Sewell, both of Kings Lynn, United Kingdom

[73] Assignee: The Dow Chemical Company, Midland, Mich.

[21] Appl. No.: 622,931

[22] Filed: Jun. 21, 1984

Related U.S. Application Data

[63] Continuation of Ser. No. 404,029, Aug. 2, 1982, abandoned.

[51] Int. Cl.$^3$ .................. C07C 118/00; C07C 127/22; C07D 213/30; C07D 213/32
[52] U.S. Cl. .................. 564/44; 260/453 P; 260/465 D; 546/290; 546/291
[58] Field of Search .............. 260/453 P, 465 D; 564/44; 546/300, 290, 291

[56] References Cited

U.S. PATENT DOCUMENTS 3,261,865  7/1966  Speziale et al. .................. 564/44
3,748,356  7/1973  Wellinga et al. .................. 564/44
3,823,144  7/1974  Schmitt et al. .................. 564/44 X

FOREIGN PATENT DOCUMENTS 1460419  1/1977  United Kingdom .
1460410  1/1977  United Kingdom .
1488644  10/1977  United Kingdom .
1492365  11/1977  United Kingdom .
1492364  11/1977  United Kingdom .
1501607  2/1978  United Kingdom .

OTHER PUBLICATIONS

Hill et al., JACS, 62, 1595-1596 (1940).

Primary Examiner—Thomas A. Waltz
Attorney, Agent, or Firm—S. Preston Jones; Ronald G. Brookens

[57] ABSTRACT

A process for preparing a benzoylphenylurea which comprises reacting a benzoyl chloride with an alkali metal cyanate in the presence of a catalyst and an inert solvent to prepare a benzoyl isocyanate which is treated in situ with an appropriate aniline compound.

11 Claims, No Drawings

METHOD FOR MAKING BENZOYLPHENYLUREAS

This is a continuation of application Ser. No. 404,029, filed Aug. 2, 1982, now abandoned.

This invention relates to a method for making benzoylphenylureas and, more particularly, relates to a novel process comprising reacting a benzoyl chloride with an alkali metal cyanate to prepare a benzoyl isocyanate which is then treated in situ with an appropriate aniline compound to give the desired benzoylphenylurea.

More specifically, the present invention comprises a process for making a compound having the formula

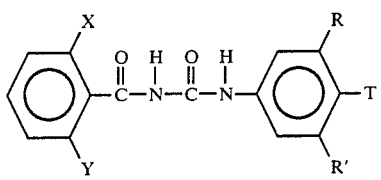

wherein each X and Y are independently —H, —F, —Cl, alkyl or haloalkyl of 1 to 6 carbon atoms; R and R' are individually —H, halogen, alkyl of 1 to 6 carbon atoms, haloalkyl of 1 to 6 carbon atoms, alkoxy of 1 to 6 carbon atoms, haloalkoxy of 1 to 6 carbon atoms, nitro or cyano wherein T is halogen, halogenated alkyl of 1 to 6 carbon atoms or the group —ZR" wherein R" is H, alkaryl, alkyl, halogenated alkyl, halogenated alkylene, pyridyl, substituted pyridyl, phenyl or substituted phenyl and Z is O or S, which comprises reacting a benzoyl chloride with an alkali metal cyanate in the presence of a catalyst and an inert solvent to prepare a benzoyl isocyanate which is treated in situ with an appropriate aniline compound.

In the present specification and claims, the terms "alkyl", "alkoxy", "haloalkyl" and "haloalkoxy", are employed to designate alkyl, alkoxy, haloalkyl or haloalkoxy groups containing from 1 to 6 carbon atoms and preferably from 1 to 4 carbon atoms.

The term "haloalkylene" is employed to designate a haloalkylene group containing from 2 to 6 carbon atoms and preferably from 2 to 4 carbon atoms.

The terms "haloalkyl", "haloalkoxy" and "haloalkylene" are further employed to designate haloalkyl, haloalkoxy and haloalkylene groups containing from 1 up to 7 chloro, bromo, fluoro or iodo atoms.

The term "halogen" is employed to designate a bromo, chloro or fluoro atom.

The term "substituted phenyl" is employed to designate a phenyl group corresponding to the formula

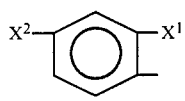

wherein $X^1$ is hydrogen, bromo, chloro or fluoro and $X^2$ is bromo, chloro, fluoro, nitro, cyano or trifluoromethyl.

The term "substituted pyridyl" is employed to designate a pyridyl group corresponding to the formula

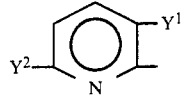

wherein $Y^1$ is hydrogen or chloro and $Y^2$ is haloalkyl, preferably trifluoromethyl.

The term "alkaryl" is employed to designate an alkyl substituted phenyl group corresponding to the formula

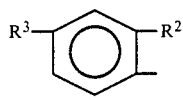

wherein $R^2$ is an alkyl group of 1 to 5 carbon atoms and $R^3$ is halogen, haloalkyl, nitro or cyano.

The compounds prepared by the method of the present invention are all known compounds useful as insecticides. The above compounds and their utility are exemplified in British Pat. Nos. 1,460,410, 1,460,418, 1,460,419, 1,488,644, 1,492,364, 1,492,365 and 1,501,607, among others.

The benzoyl chloride used in the process of this invention is advantageously prepared by the reaction of chlorine with the appropriate benzaldehyde in the presence of phosphorus pentachloride as described in British Patent Application No. 79.36243, filed Oct. 18, 1979.

The aniline compound used in the process of this invention is advantageously prepared by reacting a phenol compound having the formula

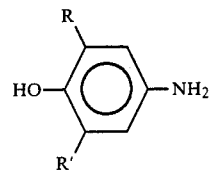

wherein R and R' are as previously described with a haloethane, haloethylene, halobenzene or a halopyridine. This reaction is preferably carried out in a polar solvent in the presence of an alkali metal base, such as sodium or potassium hydroxide, at a temperature in the range of from −20° to 220° C., more preferably at a temperature in the range of from −5° to 25° C. The preferred haloethylene is 1,1-dichloro-2,2-difluoroethylene.

While any alkali metal cyanate may be employed, the preferred cyanates are the sodium and potassium cyanates.

The preferred catalyst is cuprous chloride. The preferred solvent for use in both stages of the process of the invention is o-dichlorobenzene, xylene or chlorobenzene.

The first stage of the reaction is preferably carried out at a temperature in the range of from 100° to 200° C., more preferably at reflux temperature. The second stage of the reaction is preferably carried out at a temperature in the range of from 0° to 100° C., ambient temperature being most preferred.

The invention is further illustrated by the following examples.

EXAMPLE 1

A slurry of sodium cyanate (2.23 g) in o-dichlorobenzene (15 ml), 2-chlorobenzoyl chloride (4.61 g) and cuprous chloride (0.25 g) was prepared and heated under reflux for 40 minutes. The hot reaction mixture was filtered to remove the solids and the clear filtrate was treated with excess 4-chloroaniline. The reaction mixture was made up to a known volume with methanol and the resulting solution was assayed against an external standard showing a yield of 50 percent of N-(2-chlorobenzoyl)-N-(4-chlorophenyl)urea.

When the reaction was repeated under the same conditions using no solvent and with a reaction time of 5 to 60 minutes, no isocyanate was formed (IR). Similarly, the omission of the cuprous chloride catalyst resulted in no isocyanate being formed.

EXAMPLE 2

A slurry of potassium cyanate (2.76 g) in o-dichlorobenzene (15 ml), cuprous chloride (0.25 g) and 2-chlorobenzoyl chloride (4.61 g) was prepared and heated under reflux for 60 minutes. The solids were removed by filtration and the clear filtrate was treated with excess 4-(2,2-dichloro-1,1-difluoroethoxy)aniline. HPLC (high pressure liquid chromatography) analysis of the reaction mixture using an external standard showed a 40 percent yield of 2-chloro-N-(((4-(2,2-dichloro-1,1-difluoroethoxy)phenyl)amino)carbonyl)benzamide.

We claim:

1. A process for preparing a compound having the formula

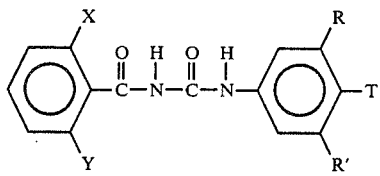

wherein X and Y are individually —H, —F, —Cl, alkyl or haloalkyl; R and R' are individually H, halogen, alkyl, haloalkyl, alkoxy, haloalkoxy, nitro or cyano; wherein T is halogen, haloalkyl or the group —ZR" wherein R" is H, alkaryl, alkyl, haloalkyl, haloalkylene, pyridyl, substituted pyridyl, phenyl or substituted phenyl and Z is O or S, which comprises reacting a benzoyl chloride with an alkali metal cyanate in the presence of a cuprous chloride catalyst and an inert solvent to prepare a benzoyl isocyanate which is treated in situ with an appropriate aniline compound.

2. A process as claimed in claim 1 wherein X and Y are individually —H, —Cl or —F; R and R' are individually —H or Cl and T is chlorine, trifluoromethyl or —ZR" wherein R" is hydrogen, chloro or fluoro substituted alkyl.

3. A process as claimed in claim 1 wherein the benzoylchloride is 2-chlorobenzoyl chloride.

4. A process as claimed in claim 1 wherein the alkali metal of the alkali metal cyanate is potassium or sodium.

5. A process as claimed in claim 1 wherein the solvent is o-dichlorobenzene.

6. A process as claimed in claim 1 wherein the reaction is carried out at reflux temperature.

7. A process as claimed in claim 1 wherein the aniline compound is 4-(2,2-dichloro-1,1-difluoroethoxy)aniline.

8. A process as claimed in claim 1 wherein the aniline is prepared by reacting a phenol compound having the formula

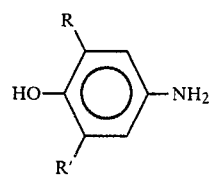

wherein R and R' are as defined in claim 1 with a haloethane, haloethylene, halobenzene or a halopyridine.

9. A process as claimed in claim 2 wherein the reaction is carried out in a polar solvent in the presence of an alkali metal base.

10. A process as claimed in claim 9 wherein the reaction is carried out at a temperature in the range of from −5° to 25° C.

11. A process as claimed in claim 8 wherein a haloethylene is employed and the haloethylene is 1,1-dichloro-2,2-difluoroethylene.

* * * * *